United States Patent
Yip et al.

(10) Patent No.: US 9,618,573 B2
(45) Date of Patent: Apr. 11, 2017

(54) TEST HANDLER THAT PICKS UP ELECTRONIC DEVICES FOR TESTING AND AN ORIENTATION-CHANGING APPARATUS FOR USE IN A TEST HANDLER

(71) Applicants: Shing Kai Yip, Kwai Chung (HK); Chi Wah Cheng, Tsing Yi (HK)

(72) Inventors: Shing Kai Yip, Kwai Chung (HK); Chi Wah Cheng, Tsing Yi (HK)

(73) Assignee: ASM TECHNOLOGY SINGAPORE PTE LTD, Singapore (SG)

( * ) Notice: Subject to any disclaimer, the term of this patent is extended or adjusted under 35 U.S.C. 154(b) by 77 days.

(21) Appl. No.: 14/603,251

(22) Filed: Jan. 22, 2015

(65) Prior Publication Data

US 2015/0204943 A1 Jul. 23, 2015

Related U.S. Application Data

(60) Provisional application No. 61/930,729, filed on Jan. 23, 2014.

(51) Int. Cl.
| | | |
|---|---|---|
| *G01R 31/01* | (2006.01) | |
| *G01R 31/28* | (2006.01) | |
| *G01R 1/067* | (2006.01) | |
| *G01R 31/26* | (2014.01) | |
| *G01R 1/00* | (2006.01) | |
| *G01N 1/00* | (2006.01) | |

(52) U.S. Cl.
CPC ..... *G01R 31/2891* (2013.01); *G01R 1/06705* (2013.01); *G01R 31/26* (2013.01); *G01R 31/2893* (2013.01); *G01N 1/00* (2013.01); *G01N 2201/00* (2013.01); *G01R 1/00* (2013.01)

(58) Field of Classification Search
CPC ........ G01N 1/00; G01N 2201/00; C12Q 1/00; C12Q 2304/00; G01R 1/00
See application file for complete search history.

(56) References Cited

U.S. PATENT DOCUMENTS

| 4,759,435 A * | 7/1988 | Cedrone | ................ | B65G 47/88 |
|---|---|---|---|---|
| | | | | 198/459.8 |
| 5,241,870 A * | 9/1993 | Holt | ..................... | B23Q 1/4828 |
| | | | | 73/866.5 |
| 5,502,397 A * | 3/1996 | Buchanan | .......... | G01R 31/2863 |
| | | | | 324/756.04 |
| 2005/0162151 A1* | 7/2005 | Tsui | .................... | G01R 31/2893 |
| | | | | 324/757.04 |
| 2010/0097075 A1* | 4/2010 | Sze | .................... | G01R 31/2893 |
| | | | | 324/555 |

* cited by examiner

*Primary Examiner* — Jermele M Hollington
*Assistant Examiner* — Temilade Rhodes-Vivour
(74) *Attorney, Agent, or Firm* — Ostrolenk Faber LLP

(57) ABSTRACT

A test handler comprises an orientation changing device having a device holder for holding electronic devices, the device holder having a vertical rotary axis. A conveying device is operative to convey electronic devices to the device holder, and a rotary motor connected to the device holder is operative to rotate the device holder about the vertical rotary axis to change an orientation of the electronic device held on it. A rotary turret of the test handler has a plurality of pick heads arranged on the rotary turret, and each pick head is configured to pick up electronic devices from the device holder.

7 Claims, 2 Drawing Sheets

TEST HANDLER THAT PICKS UP ELECTRONIC DEVICES FOR TESTING AND AN ORIENTATION-CHANGING APPARATUS FOR USE IN A TEST HANDLER

FIELD OF THE INVENTION

The present invention relates to a test handler for testing electronic devices, and in particular to a test handler incorporating an orientation-changing apparatus for the electronic devices.

BACKGROUND OF THE INVENTION

Test handlers are used in the semiconductor industry for testing electronic devices (eg. light-emitting diodes (LEDs), integrated circuits (IC) packages and semiconductor chips) by one or more test stations. It is necessary to position the electronic devices in a desired orientation before subjecting the electronic devices to testing at one or more test stations.

A vibratory bowl feeder is typically used to transport electronic devices to a test handler for testing. The vibratory bowl feeder comprises a linear track, and the orientation of the electronic devices is determined by a sensor located along the linear track. As the electronic devices are being successively conveyed by vibratory motion towards a turret handler of the test handler, the electronic devices which are found to have the desired orientation are picked up by respective pick heads of the turret handler and indexed by the test handler to one or more test stations of the test handler. The electronic devices which are found not to have the desired orientation are removed from the linear track. These electronic devices will then have to wait to be re-conveyed back onto the linear track, whereupon their orientations will again be determined by the sensor as to whether they should be transferred by the turret handler to the test station(s) for testing.

A plan view of each electronic device generally defines a rectangular shape, wherein two opposing edges are longer than another two opposing edges. When an electronic device is in the desired orientation and is picked up by the respective pick heads of the turret handler, one of the shorter edges of the electronic devices points directly towards the turret handler. In other words, the long edges of the electronic device are arranged orthogonally with respect to a circumferential path along which the turret handler rotates. Similarly, each pick head comprises a vacuum suction cavity that is also generally of a rectangular shape. However, the longer edges of the vacuum suction cavity do not correspond with the longer edges of the electronic device when the electronic device is picked up. The same applies to the shorter edges of the vacuum suction cavity. In other words, the vacuum suction cavity of each pick head is typically offset by an angle of 90 degrees with respect to each electronic device when the electronic device is picked up. Accordingly, the actual pick-up force applied on the electronic devices for the purpose of holding the electronic devices is reduced and this increases the risk of the electronic devices being dropped during transfer by the pick heads, thereby affecting the operational throughput.

SUMMARY OF THE INVENTION

Thus, it is an object of this invention to seek to address the above problem among conventional test handler, and to provide the general public with a useful choice.

According to a first aspect of the invention, there is provided a test handler comprising: an orientation changing device having a device holder for holding electronic devices, the device holder having a vertical rotary axis; a conveying device that is operative to convey electronic devices to the device holder; a rotary motor connected to the device holder which is operative to rotate the device holder about the vertical rotary axis to change an orientation of the electronic device held on it; and a rotary turret having a plurality of pick heads arranged on the rotary turret, each pick head being configured to pick up electronic devices from the device holder.

According to a second aspect of the invention, there is provided an orientation changing device for a test handler comprising a rotary turret having a plurality of pick heads arranged on the rotary turret, the orientation changing device comprising: a device holder for holding electronic devices which are received from a conveying device that is operative to convey electronic devices to the device holder, the device holder having a vertical rotary axis; a rotary motor connected to the device holder which is operative to rotate the device holder about the vertical rotary axis to change an orientation of the electronic device held on it before the electronic device is picked up by a pick head.

It would be convenient hereinafter to describe the invention in greater detail by reference to the accompanying drawings which illustrate specific preferred embodiments of the invention. The particularity of the drawings and the related description is not to be understood as superseding the generality of the broad identification of the invention as defined by the claims.

BRIEF DESCRIPTION OF THE DRAWINGS

Examples of a test handler in accordance with the invention will now be described with reference to the accompanying drawings, in which.

DETAILED DESCRIPTION OF THE PREFERRED EMBODIMENT

Figure 1:
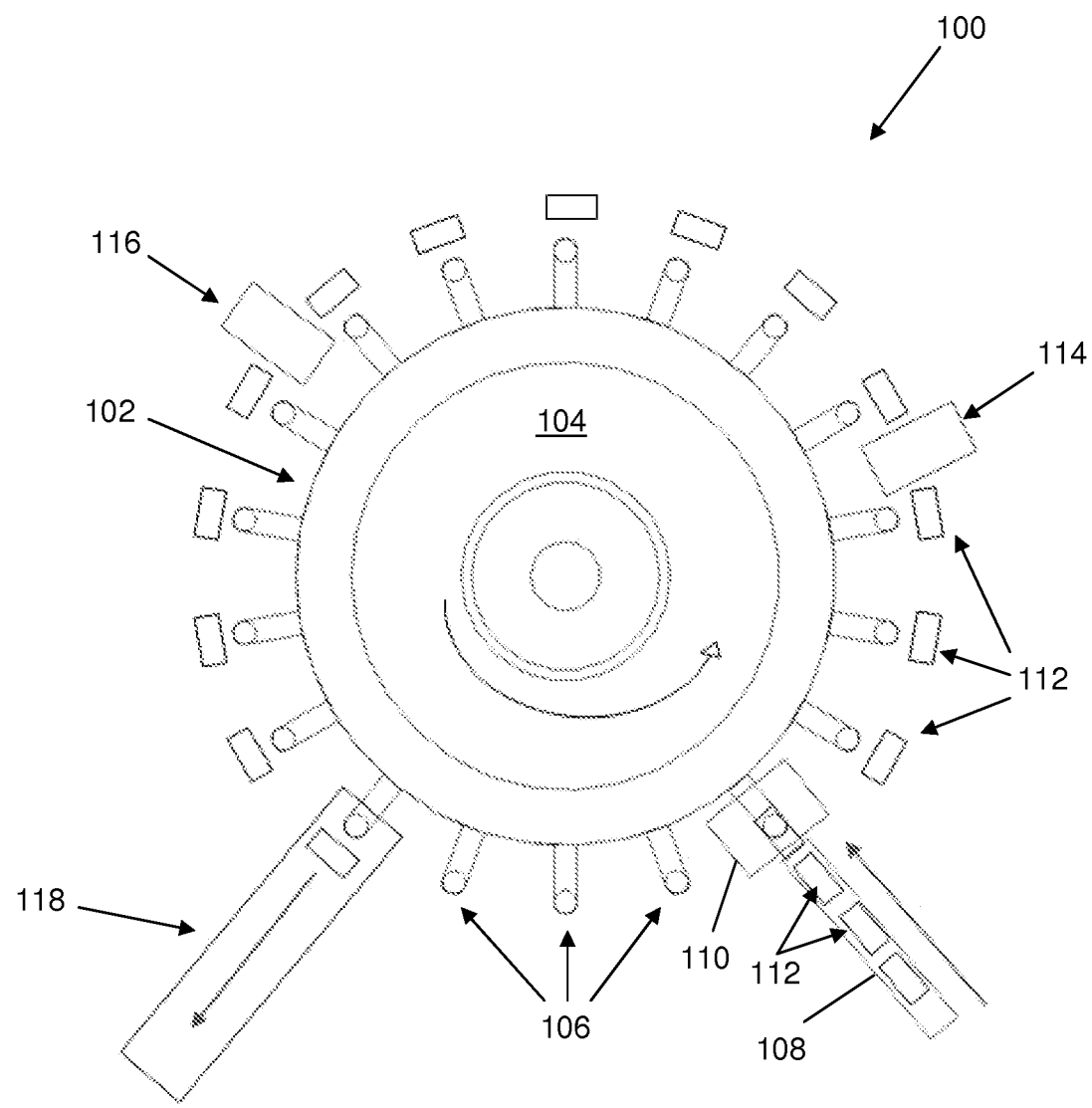
FIG. 1 is a plan view of a test handler according to the preferred embodiment of the invention.

FIG. 1 is a plan view of a test handler 100 according to the preferred embodiment of the invention. The test handler 100 comprises an orientation-changing device 110 for receiving electronic devices 112, such as IC packages and semiconductor chips. The orientation-changing device 110 receives electronic devices 112 from a conveying device, which may be in the form of a linear track 108 connected to a vibratory bowl feeder (not shown). A rotary turret handler 102 having a turret table 104 and a plurality of pick heads 106 arranged on and coupled to the turret table 104 is used for transferring the electronic devices 112 from the orientation-changing device 110 to one or more testing stations for testing, and thereafter to an output device 118 for offloading the electronic devices 112 after testing. First and second testing stations 114, 116 for receiving the electronic devices 112 which are transferred by the rotary turret handler 102 for testing are illustrated.

The pick heads 106 pick up the electronic devices 112 for transfer using vacuum suction force generated from vacuum suction cavities at the bottom of the pick heads 106. The orientation-changing device 110 is arranged adjacent to the rotary turret handler 102 at a position on a traveling path along which the plurality of pick heads 106 is moved by the turret table 104. A device holder of the orientation-changing device 110 is configured to receive electronic devices 112 individually from the linear track 108. Before each electronic device 112 is picked up by the corresponding pick head 106, the orientation-changing device 110 rotates the received electronic device 112 about a vertical axis through a required angle, such as 90 degrees, so that the orientation of the electronic device 112 is changed. Typically, the edges of the electronic devices 112 are made to align with the corresponding edges of the vacuum suction cavity of the pick head 106 for providing an optimum vacuum pick up force.

Figure 2A:
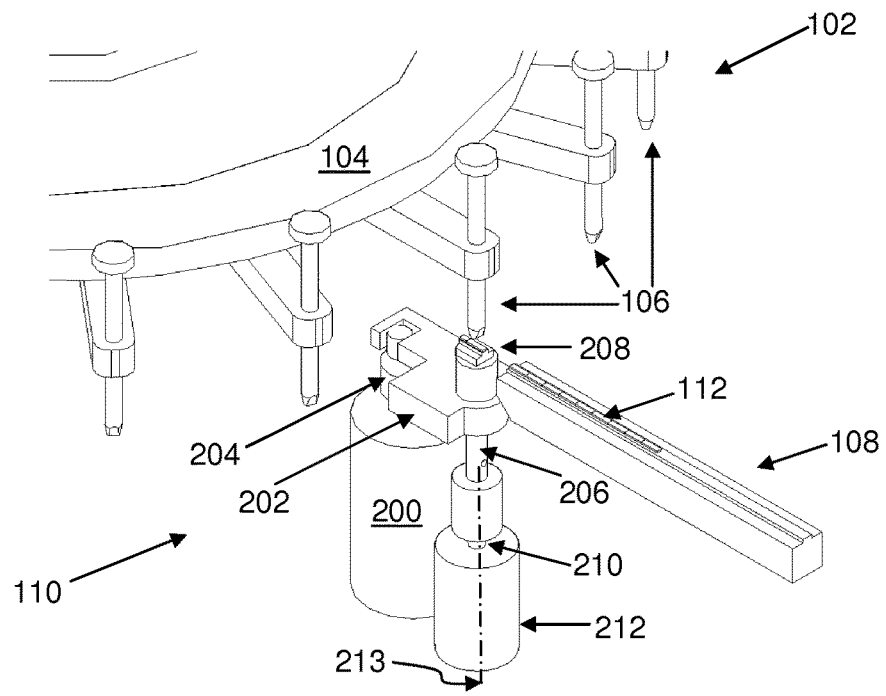
FIG. 2a is a close-up perspective view of the test handler illustrating a structure of an orientation-changing device incorporated in the test handler.

FIG. 2a is a close-up perspective view of the test handler illustrating a structure of an orientation-changing device incorporated in the test handler.

It can be seen that the orientation-changing device 110 comprises a device holder 208 for holding an electronic device 112. A cam mechanism, including a first rotary motor 200, a device holder mount (shown as a cam follower 202) and a cam 204 coupled between the first motor 200 and the cam follower 202, is arranged such that rotary motion of the first motor 200 drives the cam 204 which, in turn, translates the rotary motion of the first motor 200 into a resultant linear motion of the cam follower 202. The device holder 208 is mounted on the cam follower 202 and includes a downward-extending device shaft 206. A second rotary motor (shown as a micro servo motor 212) comprising a rotatable motor shaft 210 is coupled to the device shaft 206 to connect the micro servo motor 212 to the device holder 208. The micro servo motor 212 has a vertical rotary axis 213, and the device holder 208 is thus rotatable about the rotary axis 213.

The device holder 208 may move between a first position spaced from the end of the linear track 108 for the pick heads 106 to pick up electronic devices 112 from the device holder 208, and a second position next to the end of the linear track 108 for receiving electronic devices 112. The micro servo motor 212 is mounted together with the cam follower 202 so that it is movable together with the device holder 208 during its movement between the first and second positions.

Figure 2B:
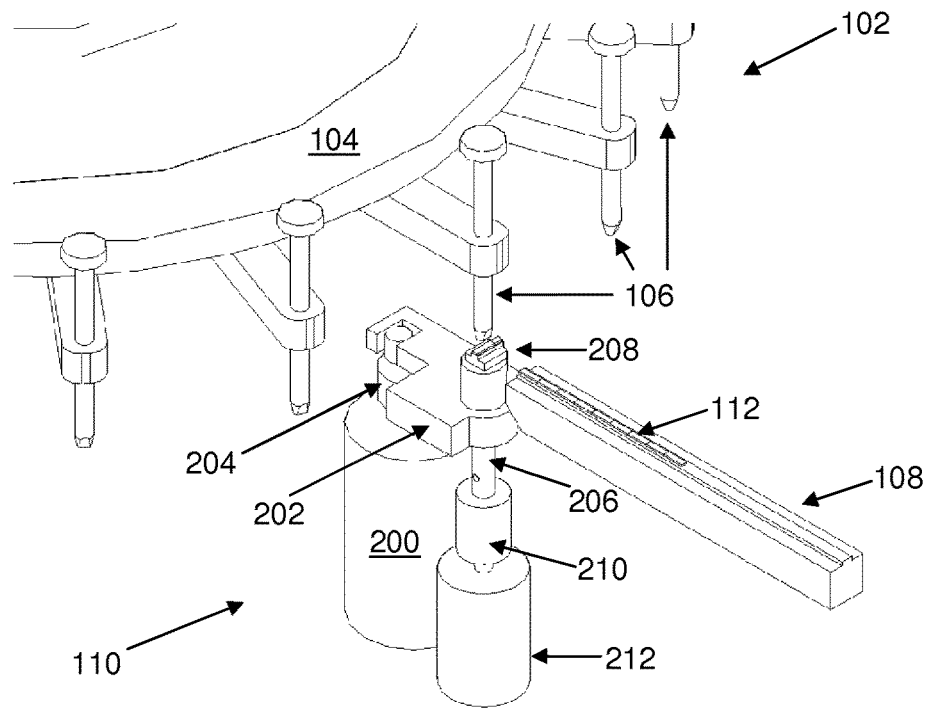
FIG. 2b illustrates the orientation-changing device of FIG. 2a wherein an orientation of an electronic device held on it has been changed.

During operation, the cam 204 is rotated by the first motor 200 to drive the cam follower 202 to move the device holder 208 to the second position of the device holder 208 next to the end of the linear track 108. This allows the device holder 208 to receive the electronic device 112 that is first in line along the linear track 108. Thereafter, the cam 204 is rotated by the first rotary motor 200 in an opposite direction to reposition the device holder 208 to the first position; which is underneath a corresponding pick head 106. Before the received electronic device 112 is picked up by a corresponding pick head 106, the motor shaft 210 is rotated by the micro servo motor 212 to drive the motor shaft 210 and the device holder 208 in a synchronized rotary motion. Consequently, the orientation of the electronic device 112 that is held on the device holder 208 is changed. Specifically, the electronic device 112 may be rotated through an angle of 90 degrees so that the orientation of its opposing edges along its length are aligned with the corresponding opposing edges of a length of the vacuum suction cavity of the pick head 106 to provide for an optimum vacuum pick up force. FIG. 2b illustrates the orientation-changing device 110 of FIG. 2a wherein an orientation of an electronic device 112 held on it has been changed. The pick head 112 will then pick up the electronic device 112 from the device holder 208.

Various other embodiments can also be envisaged within the scope of this invention. For instance, the device holder 208 may be configured to receive a plurality of electronic devices 112 from the linear track 108 instead of just a single electronic device 112 by providing the relevant mechanisms on the orientation-changing device 110. Further, the test handler 100 may also include a plurality of orientation-changing devices 110 for changing the orientation of the electronic devices 112 at multiple locations. The orientation-changing device 110 may also rotate the electronic devices 112 through any angle, and is not necessarily limited to rotation by 90 degrees.

The invention described herein is susceptible to variations, modifications and/or additions other than those specifically described and it is to be understood that the invention includes all such variations, modifications and/or additions which fall within the spirit and scope of the above description.

The invention claimed is:

1. A test handler comprising:
   an orientation changing device comprising a device holder configured to hold electronic devices, the device holder having a vertical rotary axis;
   a rotary turret comprising a plurality of pick heads arranged on the rotary turret, each pick head being configured to pick up electronic devices from the device holder at a first position;
   a conveying device positioned and configured to convey electronic devices to the device holder at a second position;
   a rotary motor connected to the device holder, the rotary motor configured to rotate the device holder about the vertical rotary axis to change an orientation of the electronic device held on the device holder; and
   a mechanism positioned and configured to drive the device holder between the first position spaced from the conveying device, and the second position next to the conveying device.

2. The test handler as claimed in claim 1, further comprising a cam follower on which the device holder is mounted, and a cam mechanism operative to drive the device holder between the first position spaced from the conveying device, and the second position next to the conveying device.

3. The test handler as claimed in claim 2, wherein the plurality of pick heads pick up electronic devices from the device holder at the first position, and the device holder receives electronic devices from the linear track at the second position.

4. The test handler as claimed in claim 2, wherein the rotary motor is connected to the device holder by a shaft, and the rotary motor is mounted together with the cam follower such that the rotary motor is movable together with the device holder.

5. The test handler as claimed in claim 1, wherein the device holder is operative to rotate the electronic device to align opposing edges along a length of the electronic device with corresponding opposing edges along a length of a vacuum suction cavity of each pick 30 head.

6. The test handler as claimed in claim 5, wherein the device holder rotates the electronic device by 90 degrees.

7. An orientation changing device for a test handler comprising a rotary turret having a plurality of pick heads arranged on the rotary turret, the orientation changing device comprising:

a device holder configured to hold electronic devices received from a conveying device that is operative to convey the electronic devices to the device holder at a first position, the device holder having a vertical rotary axis;

a rotary motor connected to the device holder, the rotary motor configured to rotate the device holder about the vertical rotary axis to change an orientation of the electronic device held on the device holder before the electronic device is picked up by a pick head at a second position;

wherein the device holder is positioned and configured to be moved between the first position next to the conveying device and the second position spaced from the conveying device.

* * * * *